United States Patent
Ha et al.

(10) Patent No.: US 10,786,602 B2
(45) Date of Patent: Sep. 29, 2020

(54) METHOD FOR TREATING SURFACE OF IMPLANT

(71) Applicant: OSSTEMIMPLANT Co., Ltd., Seoul (KR)

(72) Inventors: Kyung Won Ha, Seoul (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 228 days.

(21) Appl. No.: 14/888,592

(22) PCT Filed: Sep. 24, 2013

(86) PCT No.: PCT/KR2013/008525
§ 371 (c)(1),
(2) Date: Nov. 2, 2015

(87) PCT Pub. No.: WO2014/178489
PCT Pub. Date: Nov. 6, 2014

(65) Prior Publication Data
US 2016/0058920 A1  Mar. 3, 2016

(30) Foreign Application Priority Data
May 2, 2013 (KR) .......................... 10-2013-0049617

(51) Int. Cl.
*A61L 31/14* (2006.01)
*A61L 27/06* (2006.01)
(Continued)

(52) U.S. Cl.
CPC .............. *A61L 31/14* (2013.01); *A61L 27/06* (2013.01); *A61L 27/20* (2013.01); *A61L 27/28* (2013.01);
(Continued)

(58) Field of Classification Search
CPC ............. A61L 27/22; A61L 31/14; A61F 2/02
(Continued)

(56) References Cited

U.S. PATENT DOCUMENTS 6,339,913 B1 * 1/2002 Leon Fong ......... C23C 14/5813
427/2.27
6,702,855 B1  3/2004 Steinemann et al.
(Continued)

FOREIGN PATENT DOCUMENTS

CN    1938194 A   3/2007
CN  101784237 A   7/2010
(Continued)

OTHER PUBLICATIONS

E1, Albumin Formula 1, 2017, Wikipedia Commons, https://commons.wikiepdia,org/wiki/File:Albumin_formula_1.png.*
(Continued)

*Primary Examiner* — Dah-Wei D. Yuan
*Assistant Examiner* — Andrew J Bowman
(74) *Attorney, Agent, or Firm* — Saliwanchik, Lloyd & Eisenschenk

(57) ABSTRACT

Disclosed is a method for treating a surface of an implant. The disclosed method for treating the surface of the implant comprises the steps of: coating a surface treatment composition containing an organic material having a hydrophilic group on the surface of the implant (coating step); and drying the coated surface treatment composition (drying step).

20 Claims, 4 Drawing Sheets

(51) Int. Cl.
*A61L 27/28* (2006.01)
*A61L 27/34* (2006.01)
*A61L 27/20* (2006.01)
*A61L 31/02* (2006.01)
*A61L 31/08* (2006.01)
*B05D 3/00* (2006.01)
*A61C 8/00* (2006.01)

(52) U.S. Cl.
CPC .............. *A61L 27/34* (2013.01); *A61L 31/022* (2013.01); *A61L 31/08* (2013.01); *B05D 3/007* (2013.01); *A61C 8/0013* (2013.01); *A61L 2400/18* (2013.01); *A61L 2420/02* (2013.01)

(58) Field of Classification Search
USPC .............................. 623/11.11; 427/2.26, 2.27
See application file for complete search history.

(56) References Cited

U.S. PATENT DOCUMENTS

| | | |
|---|---|---|
| 2006/159650 A1 | 7/2006 | Alegria |
| 2008/0292779 A1 | 11/2008 | Mercuri et al. |
| 2010/0136506 A1 | 6/2010 | Park |
| 2010/0168854 A1* | 7/2010 | Luers ................... A61L 27/22 623/11.11 |
| 2013/0037516 A1 | 2/2013 | Charlton et al. |

FOREIGN PATENT DOCUMENTS

| | | | | |
|---|---|---|---|---|
| CN | 101820829 A | | 9/2010 | |
| KR | 10-2002-0061371 | * | 4/2004 | ............. A61L 27/22 |
| KR | 1020040032297 A | | 4/2004 | |
| KR | 1020040067638 A | | 7/2004 | |
| KR | 100775537 B1 | | 11/2007 | |
| KR | 1020090117807 A | | 11/2009 | |
| KR | 1020100017882 A | | 2/2010 | |
| KR | 101248785 B1 | | 4/2013 | |

OTHER PUBLICATIONS

E2, Phosphate-buffered solution, 2017, Wikipedia, https://en.wikipedia.org/wiki/Phosphate-buffered_saline.*
R1, BioUltra Biological Buffers, 2002, Sigma Aldrich, pp. 1-6 (Year: 2003).*
International Search Report dated Dec. 11, 2013 in International Application No. PCT/KR2013/008525, filed Sep. 24, 2013.
Boehm, H. P., Acidic and basic properties of hydroxylated metal oxide surfaces. *Discussions of the Faraday Society*, 52 (1971): 264-275.
Berner, S., Spontaneously Formed Nanostructures on Titanium SLActive Surfaces. *European Cells and Materials,* 23(1) (2012): 25.

* cited by examiner

[Fig. 1]
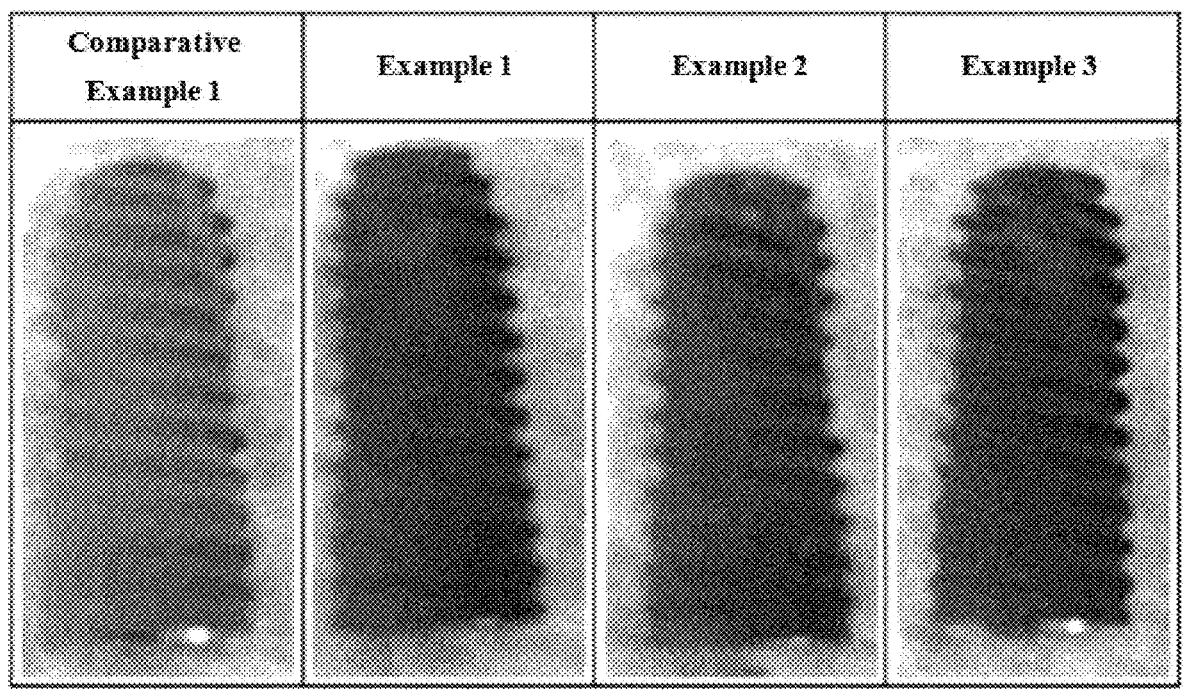

[Fig. 2]
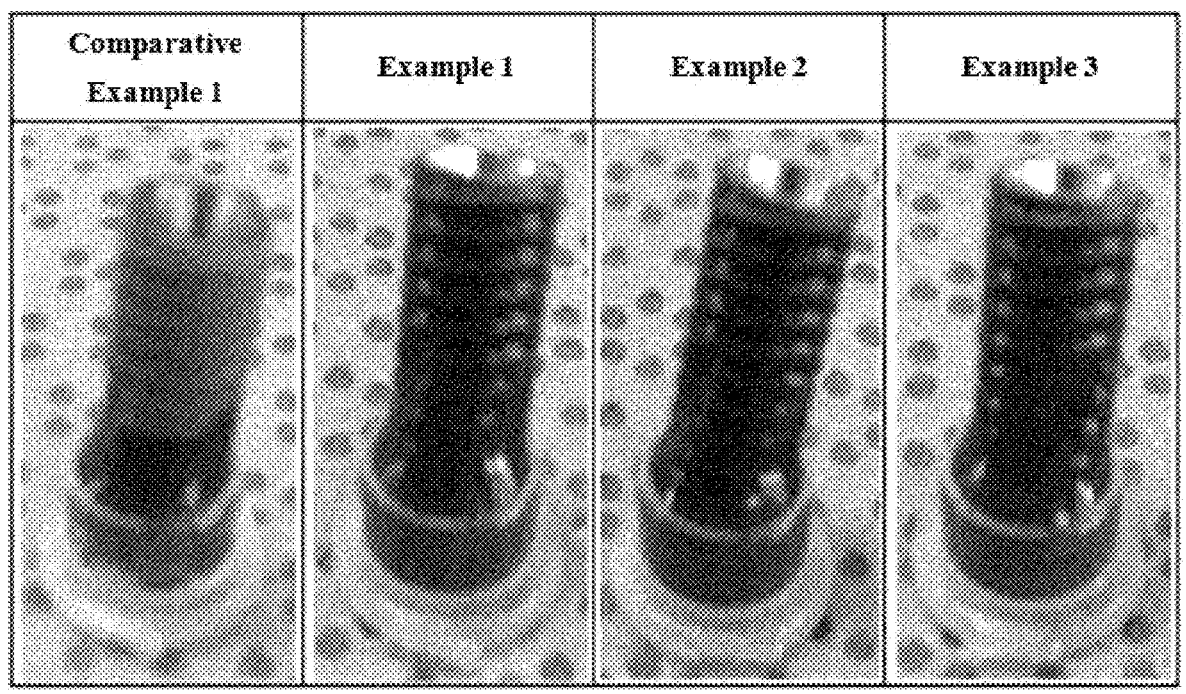

[Fig. 3]
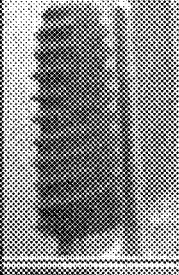

[Fig. 4]
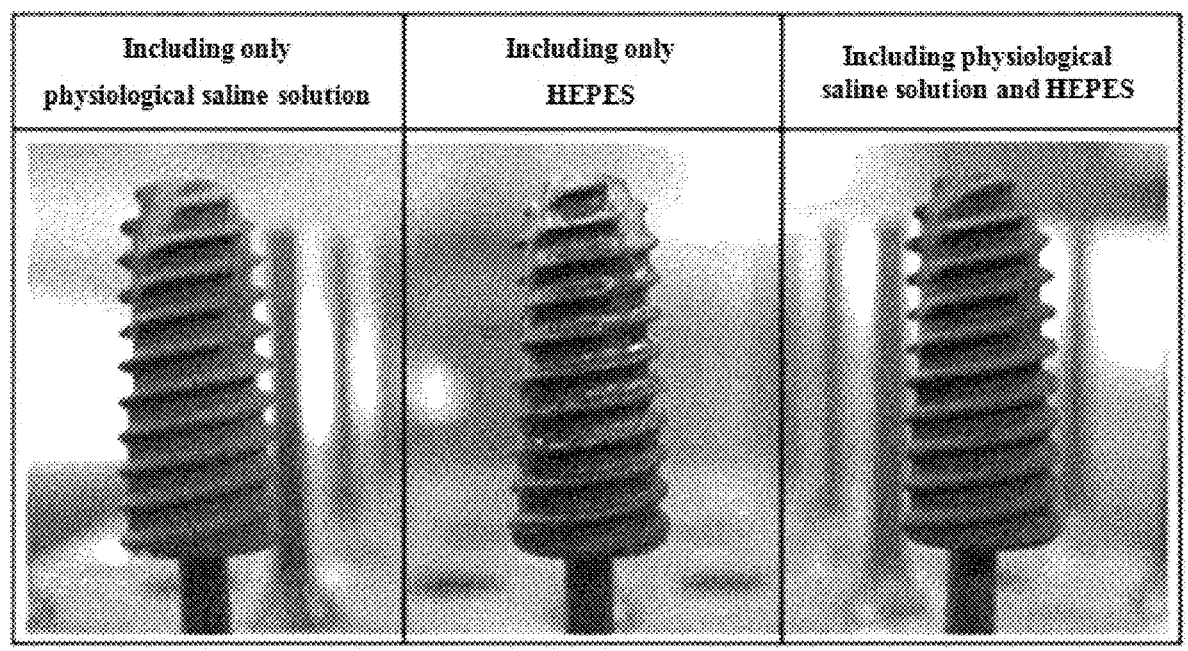

_US 10,786,602 B2_

METHOD FOR TREATING SURFACE OF IMPLANT

Cross-Reference to Related Application

This application is the U.S. national stage application of International Patent Application No. PCT/KR2013/008525, filed Sep. 24, 2013, which claims priority to Korean Application No. 10-2013-0049617, filed May 02, 2013, the disclosures of each of which are incorporated herein by reference in their entirety.

TECHNICAL FIELD

The present invention discloses a method for treating a surface of an implant. More specifically, the present invention discloses a method for treating a surface of an implant, including coating a surface treatment composition containing an organic material having a hydrophilic group on the surface of the implant.

BACKGROUND ART

There are various ways to lower the failure rate of dental implant procedures applied to living bodies and increase the fixation power with bones.

A method for strongly fixing the implant to bones mechanically by designing the implant in a screw form is generally used.

Also, a method for increasing the surface area of the implant by granting a roughness to the implant surface through sandblasting and acid etching is one of the surface treatment methods commonly applied by many implant manufacturing companies in order to achieve a strong fixation power between the implant and bone.

In addition to the above methods for strongly fixing the implant surface to bones mechanically and physically, various methods that allow bones to better adhere to the implant by coating calcium phosphate, which is an inorganic ingredient similar to human bone, on the implant surface are used.

Titanium or titanium alloy used as implant gets contaminated once it is exposed to air even after being surface treated in various manners, and thus the surface loses its activity. When the surface of titanium or titanium alloy is exposed to air or water, the surface is continuously oxidized by reacting with the surrounding oxygen (H. P. Boehm, Acidic and Basic Properties of hydroxylated Metal Oxide Surfaces, Discussions Faraday Society, vol. 52, 1971, pp. 264-275).

Among the methods for lowering the failure rate of implant procedures and obtaining stable and strong fixation power between the implant and bone, as chemical methods, there are methods for preventing contamination of implant surface or maintaining the hydrophilic property of the implant surface right after surface treatment (hereinafter, "hydrophilic property right after surface treatment"). In general, the hydrophilic property right after surface treatment gradually decreases as the implant surface is exposed to air and contaminated, and goes through continuous oxidation reaction, and in the end the surface is left with a hydrophobic property. As a method for maintaining the hydrophilic property right after surface treatment and preventing contamination of the surface, U.S. Pat. No. 6,702,855 B1 uses a method for blocking contact between air and implant by performing all processes from the step of treating the surface of the implant to the step right before transplant in an inert gas atmosphere, and using water or ion solution packing. The method of sealing by impregnating an implant in a pack filled with physiological saline solution in an inert gas atmosphere as in the above may prevent the implant from being exposed to air and be contaminated. However, the implant surface is oxidized continuously by reacting with water in the physiological saline solution, thereby forming a new oxidized layer in an embossed form on the implant surface. Due to this, there are problems that the initial quality of the implant surface right after production and the quality in the distribution process may change in the aspect of the structure of the surface and chemical property (European Cells and Materials Vol. 23. Suppl. 1, 2012, page 25). Also, since an airtight packing is required, the process is complex, the treatment cost is high, and the handling may be inconvenient.

Korean Patent Application No. 2009-7019196 discloses a method for storing an implant by using a salt-containing aqueous solution and applying gas-sealed or liquid-sealed packing as a method for maintaining the hydrophilic property of the implant surface for a long period of time. In particular, in order to maintain the hydrophilic property of the implant surface, the method suggests an inorganic salt aqueous solution of high concentration of at least 0.5 M. However, as for sodium chloride (NaCl) which takes up the greatest part of inorganic ions in human body, its concentration is 0.9 wt %, which is merely about 0.15 M when converted into mol concentration. Thus, anyone in the pertinent art may expect that an implant applied with an inorganic salt aqueous solution of high concentration of at least 0.5 M is likely to express toxicity by causing unbalance in inorganic ions in human body. Thus, in order to maintain the hydrophilic property, it is preferable not to use an inorganic salt aqueous solution of high concentration of at least 0.5 M.

Detailed Description

An embodiment of the present invention provides a method for treating a surface of an implant, including coating a surface treatment composition containing an organic material having a hydrophilic group on the surface of the implant.

Another embodiment of the present invention provides a method for treating a surface of an implant, including coating a surface treatment composition containing an organic material having a hydrophilic group and an inorganic salt on the surface of the implant.

An aspect of the present invention provides a method for treating a surface of an implant, including coating a surface treatment composition containing an organic material having a hydrophilic group on the surface of the implant (coating step), and drying the coated surface treatment composition (drying step).

The method may further include pre-treating the surface of the implant before the coating step (pre-treating step).

The pre-treating step may be performed by an operation of at least one of sandblasting, calcium phosphate coating, UV treatment, plasma treatment, acid treatment and alkali treatment.

The hydrophilic group may include at least one selected from the group consisting of a hydroxyl group (OH), a carboxyl group (COOH), an amino group ($NH_2$) and a sulfonic acid group ($—SO_3H$).

The organic material may include at least one selected from the group consisting of saccharides, proteins, acids and biological buffer or good's buffer.

The saccharides may include at least one selected from the group consisting of glucose, cellulose, alkyl cellulose, alkyl hydroxyalkyl cellulose, hydroxyalkyl cellulose, cellulose sulfate, carboxymethyl cellulose salt, carboxymethyl cellulose, carboxyethyl cellulose, chitin, carboxymethyl chitin, hyaluronic acid, hyaluronic acid salt, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenan, chitosan, starch, amylose, amylopectin, poly-N-glucosamine, polymannuronic acid, polyglucuronic acid, polyguluronic acid and derivatives of the saccharides.

The proteins may include at least one selected from the group consisting of gelatin, prothrombin, thrombin, fibrinogen, fibrin, fibronectin, heparinase, X factor, Xa factor, VII factor, VIIa factor, IX factor, IXa factor, XI factor, XIa factor, XII factor, XIIa factor, tissue factor, batroxobin, ancrod, ecarin, von Willebrand Factor, collagen, elastin, albumin, platelet surface glycoproteins, vasopressin, vasopressin analogs, epinephrine, selectin, procoagulant venom, plasminogen activator inhibitor, platelet activating factor and peptide.

The acids may include at least one selected from the group consisting of pyruvic acid, lactic acid, cysteine, glutamine, tyrosine, leucine, lycine, valine, isoleucine, threonine, phenilalanine, tryptophan, hystidine, arginine, glycine, serine, proline, glutamic acid, aspartic acid, alanine, methionine and asparagine.

The biological buffer or good's buffer may include at least one selected from the group consisting of MES (2-(N-morpholino)ethanesulfonic acid), ADA(N-(carbamoylmethyl)iminodiacetic acid), PIPES(1,4-piperazinediethanesulfonic acid), ACES(2-(carbamoylmethylamino) ethanesulfonic acid), MOPSO(3-morpholino-2-hydroxypropanesulfonic acid), cholamine chloride, MOPS (3-morpholinopropane-1-sulfonic acid), BES(N,N-bis(2-hydroxyethyl)-2-aminoethanesulfonic acid), TES(2-[[1,3-dihydroxy-2-(hydroxymethyl)propane-2-yl]amino] ethanesulfonic acid), HEPES(2-[4-(2-hydroxyethyl) piperazine-1-yl]ethanesulfonic acid), DIPSO(3-(N,N-bis[2-hydroxyethyl]amino)-2-hydroxypropanesulfonic acid), acetamido glycine, TAPSO(3-[[1,3-dihydroxy-2-(hydroxymethyl)propane-2-yl]amino]-2-hydroxypropane-1-sulfonic acid), HEPPSO(N-(2-hydroxyethyl)piperazine-N'-(2-hydroxypropanesulfonic acid), HEPPS(4-(2-hydroxyethyl)-peperazine-1-propanesulfonic acid), Tricine (N-(2-hydroxy-1,1-bis(hydroxymethyl)ethyl)glycine), glycinamide, Bicine(2-bis(2-hydroxyethyl)amino)acetic acid) and TAPS(3-[[1,3-dihydroxy-2-(hydroxymethyl)propane-2-yl]amino]propane-1-sulfonic acid).

A concentration of the organic material in the surface treatment composition may be 2,000 mM or less.

The surface treatment composition may further include an inorganic salt.

The inorganic salt may include at least one selected from the group consisting of metal chloride, metal phosphate, metal sulfate, metal carbonate and metal nitrate.

The metal in the inorganic salt may include at least one selected from the group consisting of sodium, calcium, potassium, strontium, manganese and magnesium.

A concentration of the inorganic salt in the surface treatment composition may be 200 mM or less.

The surface treatment composition may be in an aqueous solution form.

The implant may include titanium or titanium alloy.

The drying step may be performed at a temperature of 200° C. or below.

The method for treating the surface of the implant according to an embodiment of the present invention has a simple process, has low treatment cost, is easy to handle, and maintains its hydrophilic property even when packing the implant by ordinary packing.

The method for treating the surface of the implant according to another embodiment of the present invention is a method for maintaining the hydrophilic property of the surface of the implant, which preserves the hydrophilic property of the surface of the implant even without airtight packing, unlike the conventional sealing method.

BRIEF DESCRIPTION OF DRAWINGS

FIG. 1 illustrates photographs showing the difference in color between an implant which went through both pre-treatment and post-treatment (Examples 1~3), and an implant which went through only pre-treatment (Comparative Example 1);

FIG. 2 illustrates photographs showing the blood affinity of an implant which went through both pre-treatment and post-treatment (Examples 1~3), and an implant which went through only pre-treatment (Comparative Example 1);

FIG. 3 illustrates photographs showing the surface condition of an implant according to whether the surface treatment composition of the implant includes physiological saline solution, and the glucose concentration; and FIG. 4 illustrates photographs showing the surface condition of an implant according to whether the surface treatment composition of the implant includes HEPES and/or physiological saline solution.

BEST MODE FOR CARRYING OUT THE INVENTION

Hereinafter, the method for treating the surface of an implant according to an embodiment of the present invention is explained in detail.

The method for treating the surface of an implant according to an embodiment of the present invention includes (coating step) coating a surface treatment composition containing an organic material having a hydrophilic group on the surface of an implant S10, and (drying step) drying the coated surface treatment composition S20.

The implant surface may have a hydrophilic property and maintain the hydrophilic property for a long period of time by the coating step S10, and/or maintain the hydrophilic property provided in advance by the pre-treating step S1, which will be mentioned later, to the implant surface for a long period of time.

The organic material having a hydrophilic group (hereinafter, "organic material") plays the role of maintaining the hydrophilic property of the implant surface after being implanted in an alveolar bone, etc. by being left on the implant surface after surface treatment. When the implant surface maintains the hydrophilic property, the surface has high affinity with blood, allowing the entire surface to be sufficiently soaked in blood so as to quickly form new tissues on the surface, thereby and firmly binding the implant to the surrounding tissues.

The hydrophilic group may include at least one selected from the group consisting of a hydroxyl group (OH), a carboxyl group (COOH), an amino group ($NH_2$) and a sulfonic acid group ($—SO_3H$).

The organic material may be an organic material used in blood injection or cell culture.

The organic material may include at least one selected from the group consisting of saccharides, proteins, acids and biological buffer or good's buffer.

The saccharide may include at least one selected from the group consisting of glucose, cellulose, alkyl cellulose, alkyl hydroxyalkyl cellulose, hydroxyalkyl cellulose, cellulose sulfate, carboxymethyl cellulose salt, carboxymethyl cellulose, carboxyethyl cellulose, chitin, carboxymethyl chitin, hyaluronic acid, hyaluronic acid salt, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenan, chitosan, starch, amylose, amylopectin, poly-N-glucosamine, polymannuronic acid, polyglucuronic acid, polyguluronic acid and derivatives of the saccharides.

The protein may include at least one selected from the group consisting of gelatin, prothrombin, thrombin, fibrinogen, fibrin, fibronectin, heparinase, X factor, Xa factor, VII factor, VIIa factor, IX factor, IXa factor, XI factor, XIa factor, XII factor, XIIa factor, tissue factor, batroxobin, ancrod, ecarin, von Willebrand Factor, collagen, elastin, albumin, platelet surface glycoproteins, vasopressin, vasopressin analogs, epinephrine, selectin, procoagulant venom, plasminogen activator inhibitor, platelet activating factor and peptide.

The acid may include at least one selected from the group consisting of pyruvic acid, lactic acid, cysteine, glutamine, tyrosine, leucine, lycine, valine, isoleucine, threonine, phenilalanine, tryptophan, hystidine, arginine, glycine, serine, proline, glutamic acid, aspartic acid, alanine, methionine and asparagine.

The biological buffer or good's buffer may include at least one selected from the group consisting of MES(2-(N-morpholino)ethanesulfonic acid), ADA(N-(carbamoylmethyl)iminodiacetic acid), PIPES(1,4-piperazinediethanesulfonic acid), ACES(2-(carbamoylmethylamino)ethanesulfonic acid), MOPSO(3-morpholino-2-hydroxypropanesulfonic acid), cholamine chloride, MOPS(3-morpholinopropane-1-sulfonic acid), BES(N,N-bis(2-hydroxyethyl)-2-aminoethanesulfonic acid), TES(2-[[1,3-dihydroxy-2-(hydroxymethyl)propane-2-yl]amino]ethanesulfonic acid), HEPES(2-[4-(2-hydroxyethyl)piperazine-1-yl]ethanesulfonic acid), DIPSO(3-(N,N-bis[2-hydroxyethyl]amino)-2-hydroxypropanesulfonic acid), acetamido glycine, TAPSO(3-[[1,3-dihydroxy-2-(hydroxymethyl)propane-2-yl]amino]-2-hydroxypropane-1-sulfonic acid), HEPPSO(N-(2-hydroxyethyl)piperazine-N'-(2-hydroxypropanesulfonic acid), HEPPS(4-(2-hydroxyethyl)-peperazine-1-propanesulfonic acid), Tricine(N-(2-hydroxy-1,1-bis(hydroxymethyl)ethyl)glycine), glycinamide, Bicine(2-bis(2-hydroxyethyl)amino)acetic acid) and TAPS(3-[[1,3-dihydroxy-2-(hydroxymethyl)propane-2-yl]amino]propane-1-sulfonic acid).

The concentration of the organic material in the surface treatment composition may be 2,000 mM or less. In particular, the concentration of the organic material in the surface treatment composition may be greater than 0 mM and equal to or less than 2,000 mM. When the concentration of the organic material in the surface treatment composition is equal to or less than 2,000 mM, the surface treatment composition may dry well after being coated on the surface of an implant.

The surface treatment composition may further include an inorganic salt.

The inorganic salt promotes the drying of the surface treatment composition in the drying step 20, and prevents a stain from being formed on the surface of an implant after the drying step 20 by allowing the entire surface of the implant coated with the surface treatment composition to be dried in a uniform rate.

The inorganic salt may be an inorganic salt included in a physiological solution.

The inorganic salt may include at least one selected from the group consisting of metal chloride, metal phosphate, metal sulfate, metal carbonate and metal nitrate.

The metal in the inorganic salt may include at least one selected from the group consisting of sodium, calcium, potassium, strontium, manganese and magnesium.

The inorganic salt may include at least one selected from the group consisting of sodium chloride, calcium chloride, potassium chloride, strontium chloride, manganese chloride, magnesium chloride, sodium phosphate, calcium phosphate, potassium phosphate, strontium phosphate, manganese phosphate, magnesium phosphate, sodium nitrate, calcium nitrate, potassium nitrate, strontium nitrate, manganese nitrate, magnesium nitrate, sodium carbonate, calcium carbonate, potassium carbonate, strontium carbonate, manganese carbonate, magnesium carbonate, sodium sulfate, calcium sulfate, potassium sulfate, strontium sulfate, manganese sulfate and magnesium sulfate.

The concentration of the inorganic salt in the surface treatment composition may be 200 mM or less. In particular, the concentration of the inorganic salt in the surface treatment composition may be greater than 0 mM and equal to or less than 200 mM. When the concentration of the inorganic salt in the surface treatment composition is equal to or less than 200 mM, the surface treatment composition may not express cytotoxicity even after being coated on the surface of an implant.

The surface treatment composition may be in an aqueous solution form. The term "aqueous solution form" as used herein means that at least an organic material and/or an inorganic salt among the components of the surface treatment composition is present in a state dissolved in water.

For example, the surface treatment composition may be a glucose aqueous solution having a concentration of 10~200 mM.

As another example, the surface treatment composition may be an HEPES aqueous solution having a concentration of 5~150 mM.

The implant may include titanium or titanium alloy.

The solvent (e.g., water) of the surface treatment composition coated on the surface of the implant may be removed by the drying step S20, and a solid substance (i.e., organic material and/or inorganic salt) may be extracted and left on the surface of implant. As a result, an implant having a dry hydrophilic surface may be obtained.

The drying step S20 may be performed at a temperature of 200° C. or below. In particular, the drying step S20 may be performed at a temperature between −50° C. and 200° C. When the drying step S20 is performed at a temperature of 200° C. or below, in case the surface treatment composition includes an organic material, the organic material may not be oxidized. When the drying step S20 is performed by freeze-drying (−20° C.) at a temperature below zero, the hydrophilic property of the surface of an implant may be maintained.

For example, the drying step S20 may be performed at a temperature between 15~70° C. for 20 minutes~4 hours.

The method for treating the surface of the implant may further include (pre-treating step) pre-treating the surface of the implant S1 before the coating step S10.

The surface of the implant has a hydrophilic property by the pre-treating step S1.

The pre-treating step S1 may be performed by an operation of at least one of sandblasting, calcium phosphate coating, UV treatment, plasma treatment, acid treatment and alkali treatment.

The implant that goes through surface treatment by the surface treatment method may maintain a hydrophilic surface ever since surface treatment until the implant procedure is completed, even by ordinary packing, not airtight packing.

Hereinafter, the present invention will be explained in more detail with reference to the examples, but the present invention is not limited to these examples.

EXAMPLES

Examples 1~3

Pre-Treatment and Post-Treatment of Implant Surface

First, UV is irradiated on the surface of a titanium implant (self-produced) for 1 hour using a UV device (ARTEC, AH-1700) (hereinafter, "pre-treatment"). Then, after coating 10 μl of the surface treatment composition in Table 1 below on the surface of pre-treated implant, the implant coated with the surface treatment composition is first dried for 20 minutes at 25° C. and then dried for 2 hours at 60° C. (hereinafter, "post-treatment").

TABLE 1

|  | Example 1 | Example 2 | Example 3 |
| --- | --- | --- | --- |
| surface treatment composition | glucose aqueous solution of 200 mM prepared by dissolving glucose powder in distilled water | glucose aqueous solution of 150 mM prepared by dissolving glucose power in 0.9 wt % of physiological saline solution | HEPES aqueous solution of 100 mM prepared by dissolving HEPES powder in 0.9 wt % of physiological saline solution |

Comparative Example 1

Pre-Treatment of Implant Surface

The surface of the implant is pre-treated by irradiating UV on the surface of a titanium implant (self-produced) for 1 hour using a UV device (ARTEC, AH-1700). However, the steps of coating and drying the surface treatment composition of the pre-treated implant surface (i.e., post-treatment) are omitted.

EVALUATION EXAMPLES

Evaluation Example 1

Evaluation on Color of Implant Surface

Photographs showing the surface of an implant that went through only pre-treatment in Comparative Example 1, and the surface of an implant that went through both pre-treatment and post-treatment in Examples 1~3 are taken, and the result is shown in FIG. 1.

Referring to FIG. 1, it may be confirmed that the surface of an implant that went through both pre-treatment and post-treatment in Examples 1~3 changed to have a color different from the surface of an implant that went through only pre-treatment in Comparative Examples 1~3. From the above result, it may be confirmed that a solid substance (i.e., sodium chloride derived from glucose and/or physiological saline solution having hydrophilic property) is left on the surface of an implant that went through both pre-treatment and post-treatment.

Evaluation Example 2

Evaluation on Blood Affinity of Implant Surface

Photographs of each implant are taken after putting the implant that went through only pre-treatment in Comparative Example 1 and the implant that went through both pre-treatment and post-treatment in Examples 1~3 in human blood, and the result is shown in FIG. 2.

Referring to FIG. 2, it may be confirmed that the surface of an implant that went through both pre-treatment and post-treatment in Examples 1~3 has a larger area soaked in blood than the surface of an implant that went through only pre-treatment in Comparative Examples 1~3, and thus it has excellent affinity to blood.

Evaluation Example 3

Evaluation on Stain Property of Surface Treatment Composition

Photographs showing the surface condition of an implant according to whether physiological saline solution is included in the surface treatment composition of implant and the concentration of glucose are taken, and the result is shown in FIG. 3. Here, the surface treatment composition not including physiological saline solution is prepared and the surface of the implant is treated in the same manner as Example 1 (the concentration of glucose is different), and the surface treatment composition including physiological saline solution is prepared and the surface of the implant is treated in the same manner as Example 2 (the concentration of glucose is different).

Referring to FIG. 3, when using a surface treatment composition not including physiological saline solution, when the concentration of glucose is low (25~100 mM), although the upper surface and lower surface of the implant have a dark color, a band-shaped stain having a bright color is formed in the middle part. When the concentration of glucose is high (200~400 mM), it is shown that the entire surface of the implant has a dark color with no stain.

Also, referring to FIG. 3, when using a surface treatment composition including physiological saline solution, in both the cases where the concentration of glucose is low and high (25~400 mM), it is shown that the entire surface of the implant has a dark color with no stain.

From the above result, it may be confirmed that physiological saline solution (i.e., sodium chloride) prevents a stain from being formed on the surface of implant after the post-treatment step.

Evaluation Example 4

Evaluation on Drying Property of Surface Treatment Composition

Photographs showing the surface condition of an implant according to whether HEPES and/or physiological saline solution is included in the surface treatment composition of implant are taken, and the result is shown in FIG. 4. In each case of FIG. 4, except for using the following surface treatment composition, the titanium implant goes through pre-treatment and post-treatment in the same manner as in Examples 1~3.

In FIG. 4, the term "including only physiological saline solution" means using 0.9 wt % of physiological saline solution as a surface treatment composition. The term "including only HEPES" means using an HEPES aqueous solution having a concentration of 100 mM prepared by dissolving HEPES powder in distilled water as a surface treatment composition. The term "including physiological saline solution and HEPES" means using the surface treatment composition prepared in Example 3 as a surface treatment composition.

Referring to FIG. 4, when using only "physiological saline solution" as a surface treatment composition, a stain is formed on the surface of implant. When using only "HEPES" as a surface treatment composition, undried residue is present on the surface of implant. When using "physiological saline solution and HEPES" as a surface treatment composition, no stain is formed on the surface of implant and no undried residue is present.

From the above result, it may be confirmed that physiological saline solution (i.e., sodium chloride) promotes the drying of the surface treatment composition coated on the surface of an implant.

The present invention has been described with reference to the drawings and examples, but it is to be understood that the examples herein described and shown in the drawings are for illustrative purposes only and that various equivalent modifications may be made by those skilled in the art. Thus, the technical scope of the present invention is defined by the technical idea of the appended claims.

What is claimed is:

1. A method for treating a surface of an implant, comprising: coating a surface treatment composition containing an organic material having a hydrophilic group and an inorganic salt on the surface of the implant (coating step); and drying the surface treatment composition including the organic material and the inorganic salt at a temperature less than 0° C. (drying step),
   wherein the inorganic salt promotes the drying of the surface treatment composition in the drying step and allows the entire surface of the implant coated with the surface treatment composition to be dried at a uniform rate,
   wherein a concentration of the inorganic salt in the surface treatment composition is 200 mM or less,
   wherein the surface treatment composition is in an aqueous solution form,
   wherein a solid substance derived from the organic material and the inorganic salt is left on the surface of the implant by the drying step,
   wherein the method further comprises pre-treating the surface of the implant before the coating step (pre-treating step),
   wherein the pre-treating step comprises UV treatment of the surface of the implant, and
   wherein the organic material includes at least one selected from the group consisting of MES(2-(N-morpholino)ethanesulfonic acid), ADA(N-(carbamoylmethyl)iminodiacetic acid), PIPES(1,4-piperazinediethanesulfonic acid), ACES(2-(carbamoylmethylamino)ethanesulfonic acid), MOPSO(3-morpholino-2-hydroxypropanesulfonic acid), cholamine chloride, MOPS(3-morpholinopropane-1-sulfonic acid), BES(N,N-bis(2-hydroxyethyl)-2-aminoethanesulfonic acid), TES(2-[[1,3-dihydroxy-2-(hydroxymethyl)propane-2-yl]amino]ethanesulfonic acid), HEPES(2-[4-(2-hydroxyethyl)piperazine-1-yl]ethanesulfonic acid), DIPSO(3-(N,N-bis[2-hydroxyethyl]amino)-2-hydroxypropanesulfonic acid), acetamido glycine, TAPSO(3-[[1,3-dihydroxy-2-(hydroxymethyl)propane-2-yl]amino]-2-hydroxypropane-1-sulfonic acid), HEPPSO(N-(2-hydroxyethyl)piperazine-N'-(2-hydroxypropanesulfonic acid), HEPPS(4-(2-hydroxyethyl) -peperazine-1-propanesulfonic acid), Tricine(N-(2-hydroxy-1,1-bis(hydroxymethyl)ethyl)glycine), glycinamide, Bicine(2-bis(2-hydroxyethyl)amino)acetic acid), and TAPS(3-[[1,3-dihydroxy-2-(hydroxymethyl)propane-2-yl]amino]propane-1-sulfonic acid).

2. The method of claim 1, wherein the hydrophilic group includes at least one selected from the group consisting of a hydroxyl group (OH), a carboxyl group (COOH), an amino group ($NH_2$) and a sulfonic acid group ($-SO_3H$).

3. The method of claim 1, wherein the organic material further includes at least one selected from the group consisting of saccharides, proteins, and acids.

4. The method of claim 3, wherein the saccharides includes at least one selected from the group consisting of glucose, cellulose, alkyl cellulose, alkyl hydroxyalkyl cellulose, hydroxyalkyl cellulose, cellulose sulfate, carboxymethyl cellulose salt, carboxymethyl cellulose, carboxyethyl cellulose, chitin, carboxymethyl chitin, hyaluronic acid, hyaluronic acid salt, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenan, chitosan, starch, amylose, amylopectin, poly-N-glucosamine, polymannuronic acid, polyglucuronic acid, polyguluronic acid and derivatives of the saccharides.

5. The method of claim 3, wherein the proteins includes at least one selected from the group consisting of gelatin, prothrombin, thrombin, fibrinogen, fibrin, fibronectin, heparinase, X factor, Xa factor, VII factor, VIIa factor, IX factor, IXa factor, XI factor, XIa factor, XII factor, XIIa factor, tissue factor, batroxobin, ancrod, ecarin, von Willebrand Factor, collagen, elastin, albumin, platelet surface glycoproteins, vasopressin, vasopressin analogs, epinephrine, selectin, procoagulant venom, plasminogen activator inhibitor, platelet activating factor and peptide.

6. The method of claim 3, wherein the acids includes at least one selected from the group consisting of pyruvic acid, lactic acid, cysteine, glutamine, tyrosine, leucine, lycine, valine, isoleucine, threonine, phenilalanine, tryptophan, hystidine, arginine, glycine, serine, proline, glutamic acid, aspartic acid, alanine, methionine and asparagine.

7. The method of claim 1, wherein the organic material comprises HEPES(2-[4-(2-hydroxyethyl)piperazine-1-yl]ethanesulfonic acid).

8. The method of claim 1, wherein a concentration of the organic material in the surface treatment composition is 2,000 mM or less.

9. The method of claim 1, wherein the inorganic salt includes at least one selected from the group consisting of metal chloride, metal phosphate, metal sulfate, metal carbonate and metal nitrate, and
wherein the metal in the inorganic salt includes at least one selected from the group consisting of sodium, calcium, potassium, strontium, manganese, and magnesium.

10. The method of claim 1, wherein the implant comprises titanium or titanium alloy.

11. The method of claim 1, further comprising heating the surface treatment composition after the drying step (post-treatment step).

12. The method of claim 11, wherein the post-treatment step comprises heating the surface treatment composition at a temperature of 60° C.

13. A method for treating a surface of an implant, comprising: coating a surface treatment composition containing an organic material having a hydrophilic group and an inorganic salt on the surface of the implant (coating step); and drying the surface treatment composition including the organic material and the inorganic salt at a temperature less than 0° C. (drying step),
wherein the inorganic salt promotes the drying of the surface treatment composition in the drying step and allows the entire surface of the implant coated with the surface treatment composition to be dried at a uniform rate,
wherein a concentration of the inorganic salt in the surface treatment composition is 200 mM or less,
wherein the surface treatment composition is in an aqueous solution form,
wherein a solid substance derived from the organic material and the inorganic salt is left on the surface of the implant by the drying step,
wherein the method further comprises heating the surface treatment composition after the drying step (post-treatment step), and
wherein the organic material includes at least one selected from the group consisting of MES(2-(N-morpholino)ethanesulfonic acid), ADA(N-(carbamoylmethyl)iminodiacetic acid), PIPES(1,4-piperazinediethanesulfonic acid), ACES(2-(carbamoylmethylamino)ethanesulfonic acid), MOPSO(3-morpholino-2-hydroxypropanesulfonic acid), cholamine chloride, MOPS(3-morpholinopropane-1-sulfonic acid), BES(N,N-bis(2-hydroxyethyl)-2-aminoethanesulfonic acid), TES(2-[[1,3-dihydroxy-2-(hydroxymethyl)propane-2-yl]amino]ethanesulfonic acid), HEPES(2-[4-(2-hydroxyethyl)piperazine-1-yl]ethanesulfonic acid), DIPSO(3-(N,N-bis[2-hydroxyethyl]amino)-2-hydroxypropanesulfonic acid), acetamido glycine, TAPSO(3-[[1,3-dihydroxy-2-(hydroxymethyl)propane-2-yl]amino]-2-hydroxypropane-1-sulfonic acid), HEPPSO(N-(2-hydroxyethyl)piperazine-N'-(2-hydroxypropanesulfonic acid), HEPPS (4-(2-hydroxyethyl)-peperazine-1-propanesulfonic acid), Tricine(N-(2-hydroxy-1,1-bis(hydroxymethyl)ethyl)glycine), glycinamide, Bicine(2-bis(2-hydroxyethyl)amino)acetic acid), and TAPS(3[[1,3-dihydroxy-2-(hydroxymethyl)propane-2-yl]amino]propane-1-sulfonic acid).

14. The method of claim 13, wherein the post-treatment step comprises heating the surface treatment composition at a temperature of 60° C.

15. The method of claim 13, wherein the post-treatment step comprises heating the surface treatment composition at a temperature of 60° C. for 2 hours.

16. The method of claim 13, further comprising pre-treating the surface of the implant before the coating step (pre-treating step),
wherein the pre-treating step comprises at least one of sandblasting, calcium phosphate coating, plasma treatment, acid treatment, and alkali treatment.

17. The method of claim 13, wherein the hydrophilic group includes at least one selected from the group consisting of a hydroxyl group (OH), a carboxyl group (COOH), an amino group ($NH_2$), and a sulfonic acid group ($-SO_3H$), and
wherein the organic material further includes at least one selected from the group consisting of saccharides, proteins, and acids,
wherein a concentration of the organic material in the surface treatment composition is 2,000 mM or less,
wherein the inorganic salt includes at least one selected from the group consisting of metal chloride, metal phosphate, metal sulfate, metal carbonate, and metal nitrate, and
wherein the metal in the inorganic salt includes at least one selected from the group consisting of sodium, calcium, potassium, strontium, manganese, and magnesium.

18. The method of claim 13, wherein the implant comprises titanium or titanium alloy.

19. The method of claim 13, wherein the organic material comprises HEPES(2-[4-(2-hydroxyethyl)piperazine-1-yl]ethanesulfonic acid).

20. The method of claim 13, further comprising pre-treating the surface of the implant before the coating step (pre-treating step),
wherein the pre-treating step comprises at least one of calcium phosphate coating and alkali treatment.

* * * * *